United States Patent [19]
Raleigh et al.

[11] Patent Number: 5,393,452
[45] Date of Patent: Feb. 28, 1995

[54] 2 IN 1 SHAMPOO SYSTEM AND CONDITIONER COMPRISING A SILICON-POLYETHER COPOLYMER

[75] Inventors: William J. Raleigh, Rensselaer; Raymond J. Thimineur, Scotia; Stanley J. Stoklosa, Clifton Park, all of N.Y.

[73] Assignee: General Electric Company, Waterford, N.Y.

[21] Appl. No.: 120,507

[22] Filed: Sep. 14, 1993

Related U.S. Application Data

[63] Continuation-in-part of Ser. No. 974,020, Nov. 9, 1992, abandoned.

[51] Int. Cl.$^6$ .................... A61K 7/075; C11D 3/37
[52] U.S. Cl. .................. 252/174.15; 252/173; 252/174.23; 252/174.24; 252/542; 252/544; 252/545; 252/546; 252/547; 252/548; 252/550; 252/551; 252/554; 252/555; 252/DIG. 2; 252/DIG. 13; 424/70.121
[58] Field of Search .............. 252/174.15, DIG. 13, 252/542, 547, 545, 174.17, 174.24, 174.23, DIG. 2; 424/70

[56] References Cited

U.S. PATENT DOCUMENTS

| | | | |
|---|---|---|---|
| 2,798,053 | 7/1957 | Brown . | |
| 3,915,921 | 10/1975 | Schlatner, Jr. . | |
| 4,374,825 | 2/1983 | Bolich, Jr. et al. | 424/70 |
| 4,387,090 | 6/1983 | Bolich, Jr. | 424/70 |
| 4,452,732 | 6/1984 | Bolich Jr. | 252/547 |
| 4,509,949 | 4/1985 | Huang et al. | 586/558 |
| 4,597,962 | 7/1986 | Grollier et al. | 424/47 |
| 4,636,329 | 1/1987 | Steuri | 252/106 |
| 4,673,568 | 6/1987 | Grollier et al. | 424/47 |
| 4,704,272 | 11/1987 | Oh et al. | 424/70 |
| 4,788,006 | 11/1988 | Bolich, Jr. et al. | 252/550 |
| 4,832,871 | 5/1989 | Scandel | 252/547 |
| 4,988,504 | 1/1991 | Zotto et al. | 424/65 |
| 4,997,641 | 5/1991 | Hartnett et al. | 424/70 |
| 5,019,376 | 5/1991 | Uick | 424/70 |
| 5,034,218 | 7/1991 | Duvel | 424/70 |
| 5,063,044 | 11/1991 | Kohl et al. | 424/70 |
| 5,078,990 | 1/1992 | Martin et al. | 424/70 |
| 5,114,706 | 5/1992 | Duvel | 424/70 |
| 5,145,607 | 9/1992 | Rich | 252/547 |
| 5,151,210 | 9/1992 | Steuri et al. | 252/174.17 |
| 5,152,914 | 10/1992 | Forster et al. | 252/174 |
| 5,292,503 | 3/1994 | Raleigh et al. | 424/59 |

*Primary Examiner*—Paul Lieberman
*Assistant Examiner*—A. Hertzog

[57] ABSTRACT

Two in one shampoo compositions and hair conditioner compositions comprising a high molecular weight, high viscosity silicone-polyether copolymer are disclosed having improved anti static properties.

37 Claims, No Drawings

5,393,452

2 IN 1 SHAMPOO SYSTEM AND CONDITIONER COMPRISING A SILICON-POLYETHER COPOLYMER

CROSS-REFERENCE TO RELATED APPLICATIONS

This application is a continuation-in-part of U.S. Ser. No. 07/974,020, filed Nov. 9, 1992, now abandoned.

FIELD OF THE INVENTION

The present invention relates to a novel shampoo composition. More particularly, the present invention relates to a novel shampoo composition having improved anti-static properties. More particularly, the present invention relates to a shampoo composition comprising a silicone-polyether copolymer in combination with a fatty alcohol, ester, or other fatty compound as an essential medium of suspension for said silicone-polyether copolymer having improved anti-static properties.

BACKGROUND OF THE INVENTION

A variety of 2 in 1 conditioning shampoos are disclosed in the prior art. These 2 in 1 shampoo compositions are desirable since they combine a cleansing function and a conditioning function into one commercial product. Accordingly, 2 in 1 shampoos now represent the most rapidly growing segment of the shampoo market.

To date the most significant technical concern exhibited by the prior art has been improving the compatibility between the cleansing surfactants and the conditioning agents. Such a concern relating to improving the compatibility between cleansing surfactants and conditioning agents is addressed by recent U.S. patents, for example U.S. Pat. No. 4,704,272 to Oh, U.S. Pat. No. 4,788,006 to Bolich, and U.S. Pat. No. 5,034,218 to Duvel.

More recently, in a commonly assigned U.S. patent application Ser. No. 07/906,978, filed Jun. 30, 1992, there is disclosed a 2 in 1 shampoo composition having enhanced silicone deposition for further improvement in conditioning properties.

A need still exists for a 2 in 1 shampoo composition having improved anti-static properties combined with the improved conditioning properties associated with a 2 in 1 shampoo composition. Applicants have developed a shampoo composition comprising a high molecular weight silicone-polyether copolymer component in combination with a fat derivative compound acting as an essential dispersing agent or carrier for the high molecular weight silicone-polyether copolymer that provides improved anti-static properties while maintaining the desirable conditioning properties of the new 2 in 1 type shampoo compositions. Such improvements are herein after demonstrated in the working examples.

SUMMARY OF THE INVENTION

According to the present invention there is provided a shampoo composition as an emulsion having improved anti-static properties while retaining good conditioning essentially comprising (a) an anionic surfactant, a nonionic surfactant, an amphoteric surfactant or mixtures thereof; (b) a suspending or dispersing agent or carrier; (c) a high molecular weight silicone ether copolymer; (d) a quaternary ammonium compound; and (e) water.

Having described an improved shampoo composition, there is also provided a method of shampooing hair comprising applying the shampoo composition of the present invention to hair and subsequently rinsing the shampoo composition from the hair.

Further, according to the teachings of the present invention, there is provided a hair conditioning composition having improved anti-static properties comprising a suspending or dispersing agent or carrier, a high molecular weight silicone ether copolymer, a quaternary ammonium compound and water.

DETAILED DESCRIPTION OF THE INVENTION

The first component of the shampoo compositions of the present invention is the surfactant or mixtures thereof which may be selected from the classes of either or both of anionic surfactants or nonionic surfactants. These surfactants, known to persons of ordinary skill in the art, include all of those commonly used in shampoos and conditioning formulations.

Typical anionic surfactants usable in the context of the present invention include alkyl and alkyl ether sulfates having the respective formulas $ROSO_3Mt$ and $RO(C_2H_4O)_zSO_3Mt$ wherein R is alkyl or alkenyl of from about 10 to about 20 carbon atoms, z ranges from 1 to about 10, and Mt is a water soluble monovalent cation preferably an alkali metal cation, an ammonium cation, a substituted ammonium cation or triethanolamine as a cation. The alkyl ether sulfates useful in the practice of the present invention are condensation products of ethylene oxide and monohydric alcohols having from about 10 to about 20 carbon atoms. Preferably, R has from about 14 to about 18 carbon atoms in both the alkyl and the alkyl ether sulfates. The alcohols may be derived from fats such as coconut oil or tallow, or they may be synthetic. In the practice of the present invention, lauryl alcohol and straight chain alcohols derived from coconut oil are preferred herein. Such alcohols are reacted with from about 1 to about 10, and particularly 3, moles of ethylene oxide and the resulting mixture of molecular species, having, for example, an average of 3 moles of ethylene oxide per mole of alcohol is subsequently sulfated and neutralized.

Specific examples of alkyl ether sulfates useful in the practice of the present invention include but are not limited to sodium coconut alkyl trioxyethylene sulfate, lithium tallow alkyl trioxyethylene sulfate, and sodium tallow alkyl hexaoxyethylene sulfate. More preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such mixture also comprises from about 0 to about 20% by weight $C_{12-13}$ compounds; from about 60 to 100% by weight of $C_{14-16}$ compounds; from about 0 to 20% by weight of $C_{17-19}$ compounds where the degree of ethoxylation also varies, from about 3 to about 30% by weight of compounds having a degree of ethoxylation of 0%, from bout 45 to 90% by weight of compounds having a degree of ethoxylation ranging from about 1 to about 4; from about 10 to about 25% by weight of compounds having a degree of ethoxylation ranging from about 4 to about 8; and from about 0.1 to about 16% by weight of compounds having a degree of ethoxylation greater than about 8.

Additional examples of anionic surfactants coming within the terms of the present invention are the reaction products of fatty acids esterified with isothionic acid and neutralized with sodium hydroxide wherein, for example, the fatty acids are derived from coconut oil; alkali metal salts, e.g. sodium and potassium, of fatty acid amides of methyl lauride in which for example the fatty acids are derived from coconut oil. Other anionic surfactants of this type are described in U.S. Pat. Nos. 2,486,921; 2,486,922; and 2,396,278; in the patent art cited these anionic surfactants are called anionic synthetic detergents. In the context of textile processing, these materials described by the above cited patents are detergents, in the context of shampoos these materials are surfactants.

Other synthetic detergents include the class designated as succinamates. This class includes among others disodium N-octyadecylsulfosuccinamate; tetra sodium N-(1,2-dicarboxyethyl)-N-octadecylsulfosuccinamate; dihexyl sulfosuccinamate (the dihexyl ester of sodium sulfosuccinic acid); dioctyl sulfosuccinamate (the dioctyl ester of sulfosuccinic acid); and mixtures thereof.

Still other suitable anionic surfactants that may be utilized in the context of the present invention are olefin sulfonates having from about 12 to about 24 carbon atoms. The term "olefin sulfonates" is hereby defined to mean compounds that can be produced by the sulfonation of alpha-olefins by means of uncomplexed sulfur trioxide, followed by the neutralization of the acid reaction mixture such that any sulfones that may have formed in the reaction are hydrolyzed to yield the corresponding hydroxy-alkanesulfonates. The alpha-olefins from which the olefin sulfonates are derived are mono-olefins having from about 12 to about 24 carbon atoms, preferably from about 14 to about 16 carbon atoms and are preferably straight chain olefins. Suitable examples of appropriate straight chain alpha-olefins include but are not limited to 1-duodecene, 1-tetradecene, 1-hexadecene, 1-eicosene, and tetracosene. The sulfur trioxide may be either liquid or gaseous, and is usually, but not necessarily diluted by inert diluents, for example by liquid sulfur dioxide, chlorinated hydrocarbons, etc., when used in the liquid form; or by air, nitrogen, or by gaseous sulfur dioxide, etc. when used in the gaseous form. In addition to the true alkene sulfonates and a proportion of hydroxy-alkanesulfonates, the olefin sulfonates may contain minor amounts of other materials, such as alkaline disulfonates, depending upon the reaction conditions, proportions of reactants, the nature of the starting olefins, and impurities in the precursor olefin stock, and side reactions during the sulfonation process. A specific alpha-olefin sulfonate mixture of the type just described is more completely described in U.S. Pat. No. 3,332,880.

Still another class of anionic surfactants are the beta-alkyloxy alkane sulfonates. These compounds have the following formula:

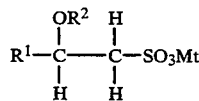

where $R_1$ is a straight chain alkyl group having from about 6 to about 20 carbon atoms, $R_2$ is a lower alkyl group having from 1 to about 3 carbon atoms, and Mt is a monovalent cation as herein before described. Specific examples of beta-alkyloxy-alkane-1-sulfonates or 2-alkyloxy-alkane-1-sulfonates include but are not limited to: potassium-beta-methoxydecanesulfonate, sodium 2-methoxytridecane sulfonate, potassium 2-ethoxytetradecylsulfonate, sodium 2-isopropoxyhexadecylsulfonate, lithium 2-t-butoxytetradecylsulfonate, sodium methoxyoctadecylsulfonate, and ammonium n-propoxydodecylsulfonate. The beta alkyloxy-alkane-1-sulfonates exhibit a low sensitivity to calcium ions (hardness sensitivity) under the conditions normally encountered in household washing and bathing and because of this low hardness sensitivity exhibit superior cleaning properties.

Still another class of anionic surfactants are water soluble alkyl sulfate salts of the general formula:

$$R^3-SO_3-Mt'$$

wherein $R^3$ is chosen from the group consisting of a straight or branched chain, saturated aliphatic hydrocarbon radical having from about 8 to about 24, preferably from about 12 to about 18, carbon atoms; and Mt' is a cation, that is not necessarily monovalent cation. Some examples of the alkyl sulfates are the methane series compounds: iso-, neo-, ineso-, and n-paraffins, having from about 8 to about 24 carbon atoms, preferably from 12 to about 18 carbon atoms. Preferred compounds are the alkali metal and ammonium sulfated $C_{12-18}$ n-paraffins. Reference is made to McCutcheon's Detergents and Emulsifiers, 1984 Annual, published by Allured Publishing Corporation and to U.S. Pat. No. 3,929,678 wherein many other useful anionic surfactants are disclosed.

The foregoing anionic surfactants can be used in combination with known nonionic surfactants or alternatively the nonionic surfactants may be used as the sole type of surfactants comprising the component (a), some examples of which are the alkanolamides and ethoxylated amides which are well-known in the art and are commercially available.

A further alternative choice is the amphoteric surfactants such as the amine oxides and the betaine compounds. These may be used either singly in combination with themselves or in combination with the other two types of surfactants suitable for use as the component (a) of the present shampoo composition.

All of the above-mentioned surfactants may be used either singly or in combination, either in homologous combination, i.e. mixtures within one class of surfactant compounds, or heterologous combination, i.e. mixtures of surfactant compounds containing more than one class of surfactant compound. The surfactant compounds suitable to comprise component (a) are the anionic, nonionic, and amphoteric surfactants. The preferred surfactants for the practice of the present invention are the alkyl sulfates, the ethoxylated alkyl sulfates, and mixtures thereof.

The second component of the shampoo compositions of the present invention are the dispersing or suspending agents, herein after referred to as suspending agents solely for the purposes of avoiding prolixity The very high molecular weight silicone-polyether copolymers require an agent to suspend them in order to be able to introduce them into a shampoo emulsion with a commercially acceptable shelf life. The suspending agent, component (b) may be selected from a wide variety of materials known in the art to be suspending or dispersing agents. As with the surfactants comprising component (a), there are three classes of suspending agents: anionic polymers, gums, and long chain aliphatic compounds, for example fatty alcohols, esters, acids and the like.

The anionic polymers used as suspending agents (b) in the present invention are the cross linked anionic polymers of acrylic or methacrylic acid derivatives, for example, acrylic acid, the alkali metal and ammonium salts of acrylic acid, methacrylic acid, the alkali metal and ammonium salts of methacrylic acid, acrylamide, methacrylamide, the N-alkyl substituted amides, the N-aminoalkylamides, the corresponding N-alkylaminoalkyl substituted amides, the aminoalkyl acrylates, the aminoalkyl methacrylamides, and the N-alkyl substituted aminoalkyl esters of either acrylic or methacrylic acids. These polymeric compositions may be homopolymers or they may be copolymers with other copolymerizing monomers known in the art. Examples of copolymerizing monomers known in the art include but are not limited to ethylene, propylene, isobutylene, styrene, alphamethylstyrene, vinyl acetate, vinyl formate, alkyl ethers, acrylonitrile, methacrylonitrile, vinyl chloride, vinylidene chloride, the alkyl acrylates, the alkylmethacrylates, the alkyl fumarates, the alkyl maleates, and other olefinic monomers copolymerizable therewith.

Another class of cross linked anionic organic polymers are the polymers of vinylsulfonic acid, and the copolymers of vinylsulfonic acid with one or more polymerizable or copolymerizable organic monomers known in the art as previously listed. The sulfonic acid groups so introduced may be converted to sulfonic acid salts, acid amides or other electrolytic groupings. The copolymers of this type may involve the use of a plurality of sulfonic acid monomers and/or a plurality of the conventional co-monomers as described.

The cross linked anionic polymers should have a weight average molecular weight of at least about 50,000, preferably at least about 150,000 and more preferably at least about 1,000,000.

Suitable commercially available anionic polymers are the cross-linked acrylic acid polymers sold under the trademark CARBOPOL ® by B. F. Goodrich. Particularly suitable are CARBOPOL ® 1382 and CARBOPOL ® 1342. These materials are further described in U.S. Pat. Nos. 4,509,949; 3,915,921; and 2,798,053.

Xanthan gum is an agent which can also be used in the shampoo compositions to suspend or disperse the high molecular weight silicone ether copolymer. This biosynthetic gum material is commercially available and is a heteropolysaccharide with a molecular weight in excess of 1,000,000. Xanthan gum contains D-glucose, D-mannose, and D-gluconorate in the molar ratio of 2.8:2.0:2.0. The polysaccharide is partially acetylated with 4.7% acetyl groups. Reference is made to Whistler, Roy, L. "Industrial Gums-Polysaccharides and Their Derivatives," New York, Academic Press, 1973. Xanthan gum is commercially available as KELTROL (R) from Kelco a division of Merck & Co., Inc. In the compositions of the present invention, the xanthan gum is typically present at a level of from about 0.2% to about 3.0% by weight, and preferably from about 0.6% to about 1.2% by weight.

Other suspending or dispersing agents are the alkanol amides of fatty acids, having from about 16 to about 18 carbon atoms. Preferred examples of such compounds are stearic monoethanolamide, stearic diethanolamide, stearic monoisopropanolamide, and stearic monoethanolamide stearate.

Still other suitable non-acyl derivative suspending or dispersing agents are $C_{16-22}$ alkyl dimethyl amine oxides such as stearyl dimethyl amine oxide.

The suspending or dispersing agent or mixture thereof is present at a level of from about 0.2 to about 5.0% by weight, preferably from about 0.5 to about 2.5% by weight. The suspending or dispersing agent is necessary to be able to incorporate the high molecular weight silicone ether copolymers essential to the shampoo composition of the present invention.

Essential to the present invention, in order to provide the improved antistatic properties, is the inclusion of component (c), high molecular weight, high viscosity silicone ether copolymers. The silicone-polyether copolymers useful in the present invention are those of the general formula:

wherein M represents an endcapping unit of the general formula $R^4{}_3SiO_{\frac{1}{2}}$, wherein each $R^4$ is the same or different and independently represents hydrogen or a monovalent substituted or unsubstituted hydrocarbon of from 1 to 30 carbon atoms; D represents a difunctional siloxy unit of the formula $R^4{}_2SiO_{2/2}$ wherein each $R^4$ is as defined above; and D' represents a difunctional siloxy of the formula $R^4R^5SiO_{2/2}$ wherein $R^4$ is as defined above, and $R^5$ is a polyalkylene ether of the formula $R^6{}_a$—$(OR^7)_n$—$OR^8$ where $R^6$ is a substituted or unsubstituted alkylene group of 1 to 20 carbon atoms, $R^7$ is generally —$CH_2CH_2$—, $R^8$ is a hydrogen atom, hydroxy or hydrocarbon radical of from 1 to about 12 carbon atoms, n has a value of from about 5 to about 20, and a is 0 or 1; and x is above about 1 and y is above about 1.

Suitable $R^4$ groups include hydrogen, alkyl such as methyl or ethyl, vinyl, phenyl, trifluoropropyl and the like. Preferably, at least 80 percent by number of all $R^4$ groups are methyl.

$R^7$ may be —$CH_2CH_2$—, —$CH_2CH(CH_3)$—, —$CH_2C(CH_3)_2$—, —$CH_2CH_2CH_2CH_2$—, etc. Preferably, however, at least 50 percent by number, and more preferably all, of the $R^7$ are —$CH_2CH_2$—.

$R^6$ is the group which bonds the polyoxyalkylene segment to the polysiloxane. Typically, this group is derived from alpha-beta unsaturated carboxylic acids or alcohols. Thus, $R^6$ may be —$CH_2CH_2CH_2$—, —$CH_2CH_2$—, $CH_2CH_2CH_2CH_2$—, —$(CH_2)_{10}(C=O)$— and the like. In preferred embodiments, $R^6$ is —$CH_2CH_2CH_2$—. Otherwise, "a" could be 0 and the segments joined by —O—, which is the product of a condensation reaction between a condensable substituent on the polysiloxane and a condensable end group on polyalkylene oxide.

$R^8$ is the terminal group of the polyalkylene ether. The type of $R^8$ is not critical and may be selected from hydrogen, ethyl, propyl, butyl, phenyl, hydroxy, alkenyl, acetyl and the like. Preferably, $R^8$ is hydrogen or hydroxy.

The values for x and y are each independently above 1 and may vary widely, such as to provide a high molecular weight copolymer, i.e., one having a weight average molecular weight of greater than about 30,000. Particularly useful are copolymers having x and y to provide a copolymer having a weight average molecular weight of greater than about 30,000, and more preferably greater than about 50,000. The ratio of x:y can also vary widely, typically ranging from about 1:1 to about 20:1, and more preferably from about 3:2 to about 4:1. A particularly useful copolymer has a weight average molecular weight of about 80,000 and a x:y ratio of about 3:1. The viscosities of these high molecular weight, high viscosity silicone ether copolymers range from about 50,000 to 150,000 centipoise, a particularly useful range is from about 60,000 to about 120,000 centipoise, and a preferred range is from about 70,000 to about 110,00 centipoise.

The manufacture of the high molecular weight, high viscosity silicone-polyether copolymers is well known and understood to those skilled in the art. Methods of preparation typically comprise preparing a hydride fluid by standard equilibration techniques of the appropriate siloxanes. However the use of high molecular weight, high viscosity silicone ether copolymers in 2 in 1 shampoo formulations has not been previously taught. Concurrently, an alpha-beta unsaturated alcohol or carboxylic acid is introduced into the polymerization of alkylene glycols to produce a terminally unsaturated polyalkylene glycol. These terminally unsaturated polyalkylene glycols are then reacted with the hydride fluid in the presence of an active metal catalyst such as a platinum catalyst to produce the high molecular weight, high viscosity silicone-polyether copolymer. See, e.g., U.S. Pat. Nos. 4,265,878; Re 25,727; 3,174,987; 4,122,029; and 3,172,899.

When the high molecular weight silicone ether copolymers used in the compositions of the present invention are synthesized they are generally prepared in a liquid hydrocarbon reaction medium such as toluene. If no precautions are taken in the preparation of the silicone ether copolymer and the hydrocarbon solvent is merely removed by evaporation or another separation process known in the art, the silicone ether copolymer so prepared, according to the teachings herein recited, will exhibit a tendency to either gel or cross link as the quantity of the hydrocarbon solvent is reduced during the process of isolating the silicone ether copolymer. If the silicone ether copolymer is successfully isolated, it is by virtue of its high molecular weight difficult to process and incorporate into shampoos and hair care compositions. The particular problems experienced with these high molecular weight silicone ether copolymers are that the high molecular weight silicone ether copolymers are not soluble at room temperature. The very high viscosity resulting from and usually associated with high molecular weight tends to prevent emulsification, thus preventing a convenient formulation of the shampoos and hair care products utilizing these high molecular weight silicone-polyether copolymers.

If during the processing of the silicone ether copolymer while the mixture is hot, a suspending or dispersing agent is added prior to the removal of the hydrocarbon solvent used for the preparation of the silicone ether copolymer, then after the solvent is removed and the mixture is cooled a dispersion or suspension of silicone ether copolymer in the suspending or dispersing agent results. The resulting suspension or dispersion is significantly easier to process and emulsify into an acceptable shampoo or hair care product. The prior art according to Zotto's U.S. Pat. No. 4,988,504 and Gee's U.S. Pat. No. 4,122,029 teaches that high molecular weight silicones may be dispersed in generic cyclic siloxanes which will function as a solvent, carrier, dispersing or suspending agent. These particular suspending or dispersing agents are not particularly effective because the cyclic siloxanes are defoaming agents for the surfactants used in the compositions of the present invention. While there are alternative carriers, suspending, or dispersing agents such as liquid hydrocarbons, these materials are unacceptable in a cosmetic product application.

The high molecular weight silicone ether copolymers are desirable in shampoos and hair care compositions because they exhibit a better lubricity in thin films thus imparting an improved combability, both wet and dry, to the hair; and when the high molecular weight silicone is a silicone-polyether copolymer, as in the case of the present invention, improved anti-static properties also result. The molecular weight ranges for the silicone ether copolymer are from about 30,000 to about 150,000 weight average, more preferably from about 60,000 to about 120,000 weight average, and most preferably from about 70,000 to about 90,000 weight average.

Another component of the compositions of the present invention are the quaternary compounds (d). Any of the known quaternary agents can be employed in the compositions of the present invention.

The quaternary compounds (d) may include a cationic water-insoluble, emulsifiable compound, such as an oil-soluble, water-dispersible di-long chain alkyl quaternary ammonium salt, particularly a di-long chain alkyl, di-short chain quaternary ammonium salt. Particularly useful are quaternary ammonium compounds having two long chain alkyl groups including from about 12 to about 22 carbon atoms. The long chains can be predominantly 12, 14, 16, 18, 20 and/or 22 carbon atoms in length and can be only one chain length or can be mixed chain lengths. The remaining two substitutions present on the quaternary nitrogen of the quaternary ammonium compound can be hydrogen; benzyl; short chain alkyl groups having 1 to 4 carbon atoms such as methyl, ethyl or hydroxyethyl; or combinations thereof, as long as the quaternary ammonium compound is oil-soluble and water-dispersible and contains two long chain alkyl substitutions, as defined. The anion of the oil-soluble quaternary ammonium compound can be any anion, such as chloride, bromide, methyl sulfate, acetate, phosphate or nitrate, as long as the quaternary ammonium compound is oil-soluble.

Quaternary agents of this type include, but are not limited to: distearyldimethylammonium chloride, dicetyldimethylammonium bromide, dimethyldi(hydrogenated tallow)ammonium chloride, dibehenyl dimonium sulfate, hydroxypropyl bis-stearylammonium chloride, and the like. See, Duvel, U.S. Pat. No. 5,034,218.

The quaternary compound may alternatively comprise a tri long chain alkyl mono short chain alkyl quaternary ammonium salt or a tri long chain amine. The long chains typically comprise from about 8 to about 22 carbon atoms, and the short chain includes alkyls having from about 1 to about 4 carbon atoms. A preferred material is tricetyl methyl ammonium chloride. Other halides such as bromide and iodide or organic groups such as methyl sulfate may be used to form the salt. Other specific compounds include tri $C_{8-10}$ methyl ammonium chloride, tri(isodecyl)amine and tri $C_{13}$ amine. See, Oh et al., U.S. Pat. No. 4,704,272.

A particularly preferred quaternary compound of the compositions of the present invention are quaternary imidazolinium compounds (d). Use of these compounds provides enhanced silicone deposition with the shampoos of the present invention. These compounds are known to those of ordinary skill in the art and are available commercially, such as Varisoft ® 475, available from Sherex Co. A particularly preferred compound is methyl-1-tallow amido ethyl-2-tallow imidazolinium methyl sulfate, commonly known by the CTFA name as Quaternium 27. While there is art teaching that the quaternary compounds are surfactants, the quaternary compounds are typically employed as conditioners or conditioning agents where they function as a deposition agent for the silicone component, depositing the conditioning silicone component upon the hair. When the quaternary compounds of the compositions of the present invention are used as emulsifiers they are used to emulsify water in oil emulsions. By contrast, the shampoo and hair conditioning products manufactured from the compositions of the present invention are oil in water emulsions, emulsions where the quaternary compounds do not function as an emulsifying agent but rather perform the function of a deposition aid for the silicone ether copolymer. Water in oil emulsions utilize lipophilic emulsifying agents, whereas in contrast oil in water emulsions utilize hydrophilic emulsifying agents. While the quaternary compounds used as deposition aids, component (d) in the compositions of the present invention, are lipophilic emulsifying agents, the emulsion system of the compositions of the present invention requires hydrophilic emulsifiers because the emulsions are water based (component (e)).

Further, in other embodiments of the present invention, it has been found that the quaternary imidazolinium compound (d) can be used in conjunction with a long chain acyl derivative, material or mixtures of such materials to obtain still further enhanced silicone conditioner deposition. Included are alkylene glycol esters of fatty acids having from about 16 to about 22 carbon atoms. Particularly useful are ethylene glycol monostearate, ethylene glycol distearate or a mixture thereof.

Water (e) is also included in the compositions of the present invention. Typically, from about 20 to about 95%, preferably from about 60 to about 85%, by weight of water is used in the shampoo compositions of the present invention.

It is also contemplated to include fatty alcohols, fatty acids, and fatty esters in the compositions of the present invention in combination with the quaternary agents (d). Particularly useful fatty alcohols are primary or secondary alcohols having from about 8 to about 32 carbon atoms, inclusive, either as single long chain lengths or as a mixture of long chain lengths in any combination. The fatty alcohols can be straight chain, branched, saturated, and/or unsaturated structures and can be used alone or in admixture with each other. The preferred fatty alcohols are straight-chained, primary alcohols having about 10 to about 26 carbons, including, but not limited to lauryl, tridecyl, myristyl, cetyl, stearyl, oleyl, behenyl, arachyl, carnubyl and ceryl alcohols and combinations thereof. Particularly useful are cetyl and stearyl alcohols.

The shampoo compositions of the present invention further provide for the addition of other hair care additives (f). These components are employed to produce the commercially acceptable embodiments of the shampoo compositions.

Such conventional ingredients are well known to those skilled in the art, e.g. preservatives such as benzyl alcohol, methyl paraben, propyl paraben and imidazolidinyl urea; cationic surfactants such as lauryl trimethyl ammonium chloride, cetyl trimethyl ammonium chloride, stearyl-dimethyl benzyl ammonium chloride and di(partially hydrogenated tallow) dimethylammonium chloride; thickeners and viscosity modifiers such as a diethanolamine of a long chain fatty acid (e.g. Cocamide MEA), amine oxides, block polymers of ethylene oxide and propylene oxide such as Pluronic ® F88 offered by BASF Wyandotte; pH adjusting agents such as mono sodium phosphate and disodium phosphate, citric acid, succinic acid, phosphoric acid, sodium hydroxide, sodium carbonate, etc.; perfumes; dyes; biocides such as Kathon ® compounds; and sequestering agents such as disodium ethylenediamine tetraacetate. Such agents are generally used individually in amounts ranging from about 0.01% to about 10%, preferably from about 0.5 to about 5% by weight of the composition.

The pH of the shampoo compositions may be in the range of from about 2.5 to about 10, and more preferably in the range of from about 4 to about 10.

The shampoo compositions of the present invention are typically prepared by conventional means, i.e., by mixing the ingredients. A preferred method is a combination of high shear and low speed blending. A more preferred method The shampoo compositions of the present invention can then be used in a method of shampooing hair comprising applying more than about 0.1 g of the shampoo composition of the present invention to hair that has been wet and then rinsing the shampoo composition out of the hair.

It is also contemplated to prepare novel creme rinses or hair conditioners having improved antistatic properties in accordance with the teachings of the present invention. These novel hair conditioners comprise a suspending agent, a silicone-polyether copolymer, a quaternary compound and water, and optional hair care additives, as defined above. They are conveniently prepared by conventional means, i.e. by mixing the ingredients. A preferred method is a combination of high shear and low speed blending.

The creme rinse compositions of the present invention can then be used in a method of hair conditioning comprising applying more than about 0.1 g of the hair conditioning compositions of the present invention to hair that has been wet, and preferably previously shampooed, and then rinsing the hair conditioning composition out of the hair.

DESCRIPTION OF EMBODIMENTS

The following examples illustrate the present invention. They are not to be construed to limit the scope of the appended claims in any manner whatsoever.

EXAMPLE A—Preparation of Copolymer A

To a 3 liter, three neck flask is added 730 grams of a hydride fluid, $MD_{400}D'_{18}M$ and 500 grams of toluene. The hydride fluid is prepared via standard acid equilibration techniques of the appropriate siloxanes, wherein M represents trimethylsiloxy, D represents dimethylsiloxy and D' represents methylhydrogensiloxy.

The mixture is heated to reflux to azeotrope dry and the contents are then cooled to below 70° C.

10 grams of 0.2N sodium acetate buffer and 0.5 grams of a platinum catalyst (Lamoreaux, U.S. Pat. No. 3,220,972) were then added and the mixture heated to 100° C. 270 grams of a commercially available polyether (Dow Chemical Company AE 501), all ethylene oxide of 550 average molecular weight, allyl initiated, hydroxy end capped, was added dropwise over a 1 hour period, maintaining the temperature at 100° C.

The reaction mixture was stirred for an additional 5 hours at 100° C. until the reaction was complete, as confirmed by infra red spectroscopy. The mixture was allowed to cool, and then 1000 grams of cetyl alcohol were added. The resulting mixture was heated to 80° C.

The mixture was then stripped of toluene by heating to a final pot temperature of 130° C. under an $N_2$ purge with 10 mm Hg vacuum overhead. A clear uniform dispersion was obtained while hot which solidifies upon cooling to room temperature.

EXAMPLE B—Preparation of Copolymer B

The procedure of Example A is followed except that stearyl alcohol is used in place of cetyl alcohol. A solid product at room temperature is formed.

EXAMPLE C—Preparation of Copolymer C

The procedure of Example B is followed except that a reactive hydride of the general formula $$MD_{800}D'_{36}M$$

is employed in forming the high molecular weight, high viscosity silicone-polyether copolymer.

EXAMPLES 1–2

Two shampoo formulations are prepared employing Copolymer A. The suspending agent, Carbopol® 1342 was dispersed in water and heated to 50° C. All other ingredients except the copolymer, quaternary agent and sodium hydroxide were then added with good mixing.

The copolymer was heated to 50° C. and added to the mixture. Stirring was continued while cooling. The quaternary agent was then added and the pH was adjusted to about 7.5 by adding the sodium hydroxide.

The results along with compositional data are set forth in Table 1 below:

TABLE 1

| | Example | |
|---|---|---|
| | 1 | 2 |
| Composition, pbw | | |
| Ammonium Laureth Sulfate[a] | 10.0 | 10.0 |
| Lauramide DEA[b] | 4.0 | 4.0 |
| Copolymer A | 4.0 | 4.0 |
| Quaternium 27[c] | 0.75 | — |
| Carbopol 1342[d] | 0.80 | 0.80 |
| 50% NaOH[e] | 0.65 | 0.65 |
| Kathon CGII[f] | 0.10 | 0.10 |
| Water | to 100 | to 100 |
| Properties | | |
| Viscosity, Cps | 5650 | 5250 |

[a]Primary surfactant, available from Stepan Co.
[b]Secondary surfactant, available from Stepan Co.
[c]CTFA name for methyl-1-tallow amide ethyl-2-tallow imidazolinium methyl sulfate, Varisoft® 475 available from Sherex Corp.
[d]Suspending agent, acrylic resin, available from B. F. Goodrich Co.
[e]Neutralizer
[f]Biocide, available from Rohm & Haas Company Both shampoo compositions exhibited excellent conditioning properties as evidenced by good wet and dry combing and excellent static control.

EXAMPLES 3–4

Two conditioner formulations were prepared according to the following. Water was heated to 60° C. and all ingredients were added with good mixing. In example 4, a small amount of citric acid was added to neutralize the amine. The mixture is cooled and pH adjusted to 4.5 with citric acid. The results along with compositional data are set forth in Table 2 below.

TABLE 2

| | Example | |
|---|---|---|
| | 3 | 4 |
| Composition, pbw | | |
| Quaternium 27[a] | 1.30 | — |
| Adogen 432[b] | — | 1.25 |
| Copolymer A | 1.25 | 1.25 |
| Copolymer B | 1.25 | 1.25 |
| Stearyl Alcohol | 1.25 | 1.25 |
| Cetyl Alcohol | 1.00 | 1.00 |
| Ceterath-20[c] | 0.50 | — |
| Stearamidopropyl diethylamine | — | 0.25 |
| Kathon CG II[d] | 0.05 | 0.05 |
| Water | to 100 | to 100 |
| Properties | | |
| Viscosity, cps | 5650 | 5250 |

[a]CTFA name for methyl-1-tallow amide ethyl-2-tallow imidazolinium methyl sulfate, Varisoft® 475 available from Sherex Corp.
[b]Quaternary dicetyl dimonium chloride, Sherex Co.
[c]Emulsifier, available from Croda, Inc.
[d]Biocide, available from Rohm & Haas Company Both conditioner compositions exhibited excellent conditioning and anti-static properties.

EXAMPLE 5

A composition according to the present invention was tested for anti-static and silicone deposition properties. For comparative properties, a similar composition without the silicone-polyether copolymer was also tested for anti-static properties.

The silicone deposition property of the composition was determined by calculating the amount of silicone deposited on the hair according to the following procedure.

5 g swatches of bleached white hair, 8 inch tresses from DeMeo Bros., Inc., New York, N.Y., were washed with a silicone free shampoo, Prell® Shampoo (Normal to Oily Hair) Procter & Gamble, Cincinnati, Ohio. The swatches were then rinsed thoroughly under warm tap water for 30 seconds to remove residual shampoo. The swatches were then hung to drip dry.

Each hair swatch was then treated with about 2 g of silicone conditioning shampoo by massaging the shampoo through the swatch for 30 seconds. The swatches were then gently rinsed under a 37° C. tap water stream for 30 seconds. The treatment and rinse were then repeated. The treated swatches were then hung to air dry for from 12 to 24 hours.

A papain enzyme solution was prepared using papain powder, 98%, from Pfaltz and Bauer, Inc., according to the procedure of E. G. Gooch and G. S. Kohl, "Method to Determine Silicones on Human Hair by Atomic Absorption Spectroscopy," J. Soc. Cosmet. Chem., 39, 383–392 (1988).

0.30±0.01 g of treated hair was then placed in a clean vial. To the vial was then added 10.0 g of the enzyme solution and the mixture was heated at 63°±3° C. for 3 days. The mixture was then extracted and decanted twice with 7.0 and 3.0 ml of methyl iso-butyl ketone, MIBK Ultrapure Reagent, J. T. Baker, Inc. The extract was then analyzed by atomic absorption spectroscopy using appropriate standards and calibration (Perkin Elmer Z-5100 PC Atomic Absorption Spectrometer). Silicone deposition was reported as parts per million by weight (ppm) silicone on the hair. The results are set forth below in Table 3.

TABLE 3

|  | Example 5 |
|---|---|
| Composition | |
| Sodium Laureth Sulfate[a] | 10.00 |
| Lauramide DEA[b] | 4.00 |
| Copolymer C | 4.00 |
| Quaternium 27[c] | 1.40 |
| Ethylene Glycol Distearate | 1.00 |
| Carbopol ® 1382[d] | 0.80 |
| 50% NaOH[e] | 0.65 |
| Kathon CG II[f] | 0.10 |
| Water | to 100 |
| Properties | |
| Viscosity, cps | 19000 |
| Deposition, ppm silicone on hair | 1150 |

[a]Primary surfactant, available from Stepan Co.
[b]Secondary surfactant, abailable from Stepan Co.
[c]CTFA name for methyl-1-tallow amide ethyl-2-tallow imidazolinium methyl sulfate, Varisoft ® 475 available from Sherex Corp.
[d]Suspending agent, acrylic resin, available from B. F. Goodrich Co.
[e]Neutralizer
[f]Biocide, available from Rohm & Haas Company As can be seen from the data in Table 3 above, the composition of the present invention exhibited excellent silicone deposition on hair. Further, no problems with fly away or static were noted in hair swatches washed with the compositions of the present invention. However, in the comparative composition which did not contain Copolymer C, static and fly away problems were noted.

EXAMPLE 6

This example demonstrates that the quaternary ammonium compound may be admixed with the fatty alcohol so that both may be added simultaneously.

PREPARATION OF FATTY ALCOHOL CARRIER

Preparation A: 270 g Alkyloxy Polyether and 500 g toluene were charged into a clean, dry vessel, neutralized with dry ice and 1% by weight of water was added. The preparation must have a haze at this point. The contents of the vessel were refluxed until all of the water was removed from the reactants by azeotropic distillation. Fuller's Earth, 1% by weight, and Celite 545, 1% by weight, were added and mixed for 15 minutes. The preparation was filtered through a Celite 545 bed and reserved for further use in the preparation of 2 in 1 shampoos.

Preparation B: 730 g of $MD_{400}D'_{18}M$ hydride fluid and 500 g toluene were charged into a clean dry vessel and heated until reflux occurred, continuing the reflux until all the water present had been removed from the reactants by azeotropic distillation. The batch was cooled to 70° C. Sodium acetate buffer, 0.1 parts by weight per weight of the mixture was added along with Platinum catalyst, 0.005 parts by weight per weight of the mixture. The temperature was adjusted to about 100° C., between 95° and 105° C.

Preparation A was slowly added to preparation B over a period of 90 minutes holding the temperature to about 100° C. After the addition of Preparation A to Preparation B was complete the mixture was agitated for a period of three hours holding the temperature at about 100° C., that is, between 95° and 105° C. After the agitation has been in progress for thirty minutes the batch should be sample for % hydrogen. If the analysis shows a hydrogen content greater than about 0.022% by weight an additional quantity of Platinum catalyst, approximately 25% more, should be charged to the mixture. When the hydrogen level was below 0.002% by weight, 1000 g stearyl alcohol was added. At the end of the stearyl alcohol addition, the mixture was vacuum distilled to remove the toluene by imposing a vacuum of 100 mm Hg and beginning heat-up. When the temperature reached 100° C. the pressure of the vacuum was reduced to 25 mm Hg. After the toluene was removed the temperature was lowered to about 70° C., that is between about 65° and about 75° C. The vacuum was broken and the product fatty alcohol carrier bottled.

PREPARATION OF FATTY ALCOHOL AND QUATERNARY ("QUAT") AMMONIUM COMPOUND BLEND

The fatty alcohol carrier and the quaternary ammonium compounds were all melted at 65° C. since all the materials are solid at room temperature.

| BLENDS | WEIGHT % |
|---|---|
| QUAT BLEND I. | |
| Fatty alcohol carrier | 89 |
| Varisoft 445 | 11 |
| (Sherex Quat, 100% active)[a] | |
| QUAT BLEND II. | |
| Fatty alcohol carrier | 89 |
| Varisoft 475 | 11 |
| (Sherex Quat, 75% active)[b] | |

[a]CTFA name for methyl-1-tallow amide ethyl-2-tallow imidazolinium methyl sulfate, Varisoft ® 445 available from Sherex Corp.
[b]CTFA name for methyl-1-tallow amide ethyl-2-tallow imidazolinium methyl sulfate, Varisoft ® 475 available from Sherex Corp.

The two mixtures I. and II. were maintained at 60° C. and agitated. After bottling and cooling the liquid suspension became a solid suspension of the fatty alcohol carrier and the quaternary ammonium compound.

A shampoo formulation using mixture I. contained 44.5% by weight silicone component, 44.5% by weight stearyl alcohol and 11% Varisoft ® 445:

| MATERIAL | PARTS BY WEIGHT |
|---|---|
| Ammonium Laureth Sulfate | 10.00 |
| Lauramide DEA | 4.00 |
| Mixture I. | 5.00 |
| Carbopol 1342 ® | 0.80 |
| 50% NAOH | 0.65 |
| Kathon CGII ® | 0.10 |
| Water | to 100 parts |

In order to make the shampoo formulation it was necessary to disperse the Carbopol 1342 ® in water at 50° C. All other ingredients were added with good mixing. The mixture was simultaneously stirred and cooled. When the mixture had cooled the pH was adjusted to about 7.5 using NaOH.

The above-mentioned patents, patent applications and publications are hereby incorporated by reference.

Many variations of the present invention will suggest themselves to those of ordinary skill in the art in light of the above-detailed description. For example, the surfactant may comprise any alkyl sulfate, ethoxylated alkyl sulfate, olefin sulfate, succinamate or beta-alkyloxyalkane sulfonate. Instead of a cross linked-acrylic resin suspending agent, xanthan gum may be employed. All such obvious modifications are within the full intended scope of the appended claims.

We claim:

1. A 2 in 1 shampoo composition having improved anti static properties comprising:

(a) an anionic surfactant selected from the group consisting of $ROSO_3Mt$ and $RO(C_2H_4O)_zSO_3Mt$ wherein R is alkyl or alkenyl of from about 10 to about 20 carbon atoms, z ranges from 1 to about 10, and Mt is a water soluble monovalent cation selected from the group consisting of alkali metal cations, ammonium cation, substituted ammonium cations or triethanolamine cation;

a nonionic surfactant selected from the group consisting of an alkanolamide and an ethoxylated amides;

an amphoteric surfactant selected from the group consisting of amine oxides and betaine compounds; used either singly in combination with themselves;

or a mixture thereof in an amount ranging up to about 14 weight percent;

(b) a suspending agent selected from the group consisting of the alkanol amides of fatty acids and alkyl dimethyl amine oxides having from about 16 to about 22 carbon atoms, and the cross linked anionic homopolymers or copolymers of vinylsulfonic acid, acrylic or methacrylic acid, acrylic acid, the alkali metal and ammonium salts of acrylic acid, methacrylic acid, the alkali metal and ammonium salts of methacrylic acid, acrylamide, methacrylamide, the N-alkyl substituted amides, the N-aminoalkylamides, the corresponding N-alkylaminoalkyl substituted amides, the aminoalkyl acrylates, the aminoalkyl methacrylamides, and the N-alkyl substituted aminoalkyl esters of either acrylic or methacrylic acids polymerized or copolymerized with monomers selected from the group consisting of ethylene, propylene, isobutylene, styrene, alpha-methylstyrene, vinyl acetate, vinyl formate, alkyl ethers, acrylonitrile, methacrylonitrile, vinyl chloride, vinylidene chloride, alkyl acrylates, alkylmethacrylates, alkyl fumarates, and alkyl maleates at a level of from about 0.2 to about 5.0% by weight;

(c) a high molecular weight, high viscosity silicone-polyether copolymer of the general formula:

$$MD_xD'_yM$$

wherein;

M is an endcapping unit of the formula $R^4_3SiO_{\frac{1}{2}}$, wherein each $R^4$ is the same or different and independently represents hydrogen or a monovalent substituted or unsubstituted hydrocarbon radical of from 1 to 30 carbon atoms;

D represents a difunctional siloxy unit of the formula $R^4_2SiO_{2/2}$ wherein each $R^4$ is as defined above; and D' represents a difunctional siloxy of the formula $R^4R^5SiO_{2/2}$ wherein;

$R^4$ is as defined above, and $R^5$ is a polyalkylene ether of the formula $R^6{}_a$—$(OR^7)_n$—$OR^8$ where $R^6$ is a substituted or unsubstituted alkylene group of from 1 to about 20 carbon atoms, $R^7$ is selected from the group consisting of —$CH_2CH_2$—, —$CH_2CH(CH_3)$—, and —$CH_2C(CH_3)_2$—;

$R^8$ is a hydrogen atom, hydroxyl or hydrocarbon radical selected from the group consisting of ethyl, propyl, butyl, phenyl, alkenyl, and acetyl;

n has a value of from about 5 to about 20, and a is 0 or 1; and x is above about 1 and y is above about 1 and the molecular weight of the silicone ether copolymer ranges from about 30,000 to about 150,000 on a weight average basis in an amount ranging from about 4 to about 44.5 weight percent;

(d) a quaternary ammonium compound selected from the group consisting of distearyldimethylammonium chloride, dicetyldimethylammonium bromide, dimethyldi(hydrogenated tallow)ammonium chloride, dibehenyl dimonium sulfate, hydroxypropyl bis-stearyl-ammonium chloride, tricetyl methyl ammonium chloride, tri-$C_{8-10}$ methyl ammonium chloride, tri(isodecyl)amine, tri-$C_{13}$ amine, and quaternary imidazolinium chlorides in an amount ranging from about 0.75 to about 1.40 weight percent; and (e) water in an amount ranging from about 20 to about 95 weight percent.

2. A shampoo composition as defined in claim 1 wherein said surfactant comprises an anionic surfactant.

3. A shampoo composition as defined in claim 2 wherein said anionic surfactant (a) is selected from the group consisting of alkyl sulfates, ethoxylated alkyl sulfates, olefin sulfates, succinamates and beta-alkyloxyalkane sulfonates.

4. A shampoo composition as defined in claim 1 wherein said suspending agent (b) comprises a cross-linked acrylic polymer.

5. A shampoo composition as defined in claim 4 wherein said cross-linked acrylic polymer comprises a polyacrylic acid or a metal salt of a polyacrylic acid.

6. A shampoo composition as defined in claim 1 wherein said high molecular, weight high viscosity silicone-polyether copolymer (c) has a weight average molecular weight of greater than about 30,000.

7. A shampoo composition as defined in claim 1 wherein said high molecular, weight high viscosity silicone-polyether copolymer (c) comprises those having the general formula:

$$MD_xD'_yM$$

wherein M represents trialkylsiloxy endcapping units of the general formula $R^4_3SiO_{\frac{1}{2}}$ where each $R^4$ is the same or different and is independently an alkyl group of from 1 to 30 carbon atoms;

D represents dialkylsiloxy units of the general formula $R^4_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula —$(R^6)_a$—$(OR^7)_n$—$OR^8$ wherein each individual $R^6$ is a substituted or unsubstituted alkylene radical having from 2 to 20 carbon atoms, $R^7$ is —$CH_2CH_2$—, $R^8$ is a hydrogen atom, hydroxy, or a hydrocarbon radical of from 1 to about 12 carbon atoms, n has a value of from about 5 to about 20, and a has a value of zero or 1;

x is above about 1; and y is above about 1, said high molecular weight high viscosity silicone-polyether copolymer having a weight average molecular weight greater than about 30,000.

8. A shampoo composition as defined in claim 7 wherein the ratio of x:y ranges from 3:2 to 4:1.

9. A shampoo composition as defined in claim 7 wherein each $R^4$ represents methyl.

10. A shampoo composition as defined in claim 1 wherein said component (c) comprises said high molecular weight, high viscosity silicone-polyether copolymer in combination with a fatty alcohol.

11. A shampoo composition as defined in claim 10 wherein said fatty alcohol comprises stearyl alcohol or cetyl alcohol or a mixture thereof.

12. A composition as defined in claim 1 wherein said quaternary compound (d) comprises a quaternary imidazolinium compound.

13. A shampoo composition as defined in claim 12 wherein said quaternary imidazolinium compound comprises methyl-1-tallow amido ethyl-2-tallow imidazolinium methyl sulfate.

14. A hair conditioning composition comprising the 2 in 1 shampoo composition as defined in claim 1 wherein said high molecular weight, high viscosity silicone-polyether copolymer comprises those having the general formula $$MD_xD'_yM$$

wherein

M represents trialkylsiloxy endcapping units of the general formula $R^4{}_3SiO_{\frac{1}{2}}$ where each $R^4$ is the same or different and is independently an alkyl group of from 1 to 30 carbon atoms;

D represents dialkylsiloxy units of the general formula $R^4{}_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula $-(R^6)_a-(OR^7)_n-OR^8$ wherein each individual $R^6$ is a substituted or unsubstituted alkylene radical having from 2 to 20 carbon atoms, $R^7$ is $-CH_2CH_2-$, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 30,000, and where the ratio of x:y varies from about 1:1 to about 20:1, said high molecular weight high viscosity silicone-polyether copolymer having a weight average molecular weight greater than about 50,000.

15. A hair conditioning composition as defined in claim 14 wherein each $R^4$ represents methyl.

16. A hair conditioning composition as defined in claim 14 wherein said high molecular weight, high viscosity silicone-polyether copolymer is employed in combination with a fatty alcohol.

17. A hair conditioning composition as defined in claim 14 wherein said quaternary compound comprises a quaternary imidazolinium compound.

18. A 2 in 1 shampoo composition having improved anti static properties consisting essentially of:
(a) an anionic surfactant, a nonionic surfactant, an amphoteric surfactant, or a mixture thereof;
(b) a suspending agent;
(c) a high molecular weight, high viscosity silicone-polyether copolymer having the general formula $$MD_xD'_yM$$

wherein

M represents trialkylsiloxy endcapping units of the general formula $R^4{}_3SiO_{\frac{1}{2}}$ where each $R^4$ is the same or different and is independently an alkyl group of from 1 to 30 carbon atoms;

D represents dialkylsiloxy units of the general formula $R^4{}_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula $-(R^6)_a-(OR^7)_n-OR^8$ wherein each individual $R^6$ is a substituted or unsubstituted alkylene radical having from 2 to 20 carbon atoms, $R^7$ is $-CH_2CH_2-$, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 30,000, and where the ratio of x:y varies from about 1:1 to about 20:1, said high molecular weight high viscosity silicone-polyether copolymer having a weight average molecular weight greater than about 50,000.

19. An improved 2 in 1 shampoo composition comprising a surfactant, a suspending agent, a quaternary compound and water, the improvement comprising an effective amount of a high molecular weight silicone ether copolymer having the general formula $$MD_xD'_yM$$

wherein

M represents trialkylsiloxy endcapping units of the general formula $R^4{}_3SiO_{\frac{1}{2}}$ where each $R^4$ is the same or different and is independently an alkyl group of from 1 to 30 carbon atoms;

D represents dialkylsiloxy units of the general formula $R^4{}_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula $-(R^6)_a-(OR^7)_n-OR^8$ wherein each individual $R^6$ is a substituted or unsubstituted alkylene radical having from 2 to 20 carbon atoms, $R^7$ is $-CH_2CH_2-$, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 30,000, and where the ratio of x:y varies from about 1:1 to about 20:1, said high molecular weight high viscosity silicone-polyether copolymer having a weight average molecular weight greater than about 50,000, in combination with a fatty alcohol, whereby the anti static properties of the shampoo composition are improved.

20. A process for making a 2 in 1 shampoo composition having improved anti static properties comprising:
(a) removing water from a terminally unsaturated polyalkylene glycol polyether;
(b) removing water from a hydride fluid, $MD_{400}D'_{18}M$, wherein M represents trialkylsiloxy endcapping units of the general formula $^4{}_3SiO_{\frac{1}{2}}$ where each $R^4$ is the same or different and is independently an alkyl group of from 1 to 30 carbon atoms; D represents dialkylsiloxy units of the general formula $R^4{}_2SiO_{2/2}$ where each $R^4$ is the same or different and is independently as defined above;

(c) reacting said polyether with said hydride in the presence of a platinum catalyst to produce a high molecular weight, high viscosity silicone-polyether copolymer having the general formula:

$$MD_xD'_yM$$

wherein M represents trialkylsiloxy endcapping units of the general formula $R^4{}_3SiO_{\frac{1}{2}}$ where each $R^4$ is the same or different and is independently an alkyl group of from 1 to 30 carbon atoms; D represents dialkylsiloxy units of the general formula $R^4{}_2SiO_{2/2}$ where each $R^4$ is the same or different and is independently as defined above; D' is an oxyalkylene siloxy unit of the general formula $R^4R^5SiO_{2/2}$ where $R^4$ is as defined above, and $R^5$ is a polyoxyalkylene ether residue of the formula —($R^6$)$_a$—($OR^7$)$_n$—$OR^8$ wherein each individual $R^6$ is a substituted or unsubstituted alkylene radical having from 2 to 20 carbon atoms, $R^7$ is —$CH_2CH_2$—, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 50,000, and where the ratio of x:y varies from about 1:1 to about 20:1

(d) adding a fatty alcohol to the high molecular weight, high viscosity silicone-polyether copolymer produced in step (c);

(e) adding a quaternary compound selected from the group consisting of distearyldimethylammonium chloride, dicetyldimethyl ammonium bromide, dimethyldi(hydrogenated tallow) ammonium chloride, dibehenyl dimonium sulfate, hydroxypropyl bis-stearyl-ammonium chloride, tricetylmethylammonium chloride, tri(isodecyl)amine, and methyl-1-tallow amido ethyl imidazolinium;

(f) adding an anionic surfactant, a nonionic surfactant, an amphoteric surfactant or a mixture thereof; and (g) adding water 21. A process for making a 2 in 1 shampoo composition having improved anti static properties comprising:

(a) removing water from a terminally unsaturated polyalkylene glycol polyether;

(b) removing water from a hydride fluid, $MD_{400}D'_{18}M$, wherein M represents trialkylsiloxy endcapping units of the general formula $^4{}_3SiO_{\frac{1}{2}}$ where each $R^4$ is the same or different and is independently an alkyl group of from 1 to 30 carbon atoms; D represents dialkylsiloxy units of the general formula $R^4{}_2SiO_{2/2}$ where each $R^4$ is the same or different and is independently as defined above;

(c) reacting said polyether with said hydride in the presence of a platinum catalyst to produce a high molecular weight, high viscosity silicone-polyether copolymer having the general formula:

$$MD_xD'_yM$$

wherein M represents trialkylsiloxy endcapping units of the general formula $R^4{}_3SiO_{\frac{1}{2}}$ where each $R^4$ is the same or different and is independently an alkyl group of from 1 to 30 carbon atoms; D represents dialkylsiloxy units of the general formula $R^4{}_2SiO_{2/2}$ where each $R^4$ is the same or different and is independently as defined above; D' is an oxyalkylene siloxy unit of the general formula $R^4R^5SiO_{2/2}$ where $R^4$ is as defined above, and $R^5$ is a polyoxyalkylene ether residue of the formula —($R^6$)$_a$—($OR^7$)$_n$—$OR^8$ wherein each individual $R^6$ is a substituted or unsubstituted alkylene radical having from 2 to 20 carbon atoms, $R^7$ is —$CH_2CH_2$—, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 50,000, and where the ratio of x:y varies from about 1:1 to about 20:1

(d) contacting a quaternary compound selected from the group consisting of distearyldimethylammonium chloride, dicetyldimethyl ammonium bromide, dimethyldi(hydrogenated tallow) ammonium chloride, dibehenyl dimonium sulfate, hydroxypropyl bis-stearyl-ammonium chloride, tricetylmethylammonium chloride, tri(isodecyl)amine, and methyl-1-tallow amido ethyl imidazolinium with a fatty alcohol;

(e) adding the product from step (d) to the high molecular weight, high viscosity silicone-polyether copolymer produced in step (c);

(f) adding an anionic surfactant, a nonionic surfactant, an amphoteric surfactant or a mixture thereof; and (g) adding water.

22. A shampoo composition as made by the process of claim 21 wherein said surfactant comprises an anionic surfactant.

23. A shampoo composition as made by the process of defined in claim 21 wherein said anionic surfactant (a) is selected from the group consisting of alkyl sulfates, ethoxylated alkyl sulfates, olefin sulfates, succinamates and beta-alkyloxyalkane sulfonates.

24. A shampoo composition as made by the process of claim 21 wherein said suspending agent (b) comprises a cross-linked acrylic resin.

25. A shampoo composition as made by the process of claim 21 wherein said cross-linked acrylic resin comprises a polyacrylic acid or a metal salt of a polyacrylic acid.

26. A shampoo composition as made by the process of claim 21 wherein said high molecular, weight high viscosity silicone-polyether copolymer (c) has a weight average molecular weight of greater than about 50,000.

27. A shampoo composition as made by the process of claim 21 wherein said high molecular weight, high viscosity silicone-polyether copolymer (c) comprises those having the general formula $$MD_xD'_yM$$

wherein

M represents trialkylsiloxy endcapping units of the general formula $R^4{}_3SiO_{\frac{1}{2}}$ where each $R^4$ is the same or different and is independently an alkyl group of from 1 to 30 carbon atoms;

D represents dialkylsiloxy units of the general formula $R^4{}_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula —($R^6$)$_a$—($OR^7$)$_n$—$OR^8$ wherein each individual $R^6$ is a substituted or unsubstituted alkylene radical having from 2 to 20 carbon atoms, $R^7$ is —$CH_2CH_2$—, $R^8$ is a hydrogen atom, hydroxy, or a hydrocarbon radical of from 1 to about 12 carbon atoms, n has a value of from about 5 to about 20, and a has a value of zero or 1;

x is above about 1; and y is above about 1, said high molecular weight high viscosity silicone-polyether copolymer having a weight average molecular weight greater than about 30,000.

28. A shampoo composition as defined in claim 27 wherein the ratio of x:y ranges from 3:2 to 4:1.

29. A shampoo composition as defined in claim 27 wherein each $R^4$ represents methyl.

30. A shampoo composition as defined in claim 27 wherein said component (c) comprises said high molecular weight, high viscosity silicone-polyether copolymer in combination with a fatty alcohol.

31. A shampoo composition as defined in claim 30 wherein said fatty alcohol comprises stearyl alcohol or cetyl alcohol or a mixture thereof.

32. A composition as defined in claim 30 wherein said quaternary compound (d) comprises a quaternary imidazolinium compound.

33. A shampoo composition as defined in claim 32 wherein said quaternary imidazolinium compound comprises methyl-1-tallow amido ethyl-2-tallow imidazolinium methyl sulfate.

34. A hair conditioning composition comprising the 2 in 1 shampoo composition as defined in claim 1 wherein said high molecular weight, high viscosity silicone-polyether copolymer comprises those having the general formula $MD_xD'_yM$ wherein M represents trialkylsiloxy endcapping units of the general formula $R^4{}_3SiO_{\frac{1}{2}}$ where each $R^4$ is the same or different and is independently an alkyl group of from 1 to 30 carbon atoms;

D represents dialkylsiloxy units of the general formula $R^4{}_2SiO_{2/2}$ where each $R^4$ is the same or different and is independently as defined above;

D' is an oxyalkylene siloxy unit of the general formula $R^4R^5SiO_{2/2}$ where $R^4$ is as defined above, and $R^5$ is a polyoxyalkylene ether residue of the formula $-(R^6)_a-(OR^7)_n-OR^8$ wherein each individual $R^6$ is a substituted or unsubstituted alkylene radical having from 2 to 20 carbon atoms, $R^7$ is $-CH_2CH_2-$, $R^8$ is a hydrogen atom, hydroxy, or a hydrocarbon radical of from 1 to about 12 carbon atoms, n has a value of from about 5 to about 20, and a has a value of zero or 1; and x and y are each above 1 and provide a copolymer having a weight average molecular weight of greater than about 30,000 and where the ratio of x:y varies from about 1:1 to about 20:1, said high molecular weight high viscosity silicone-polyether copolymer having a weight average molecular weight greater than about 30,000.

35. A hair conditioning composition as defined in claim 34 wherein each $R^4$ represents methyl.

36. A hair conditioning composition as defined in claim 34 wherein said high molecular weight, high viscosity silicone-polyether copolymer is employed in combination with a fatty alcohol.

37. A hair conditioning composition as defined in claim 34 wherein said quaternary compound comprises a quaternary imidazolinium compound.

* * * * *